(12) United States Patent
Frankard

(10) Patent No.: US 7,820,881 B2
(45) Date of Patent: Oct. 26, 2010

(54) PLANTS HAVING INCREASED YIELD AND METHOD FOR MAKING THE SAME

(75) Inventor: Valerie Frankard, Sint-Genesius-Rode (BE)

(73) Assignee: CropDesign N.V. (BE)

( * ) Notice: Subject to any disclaimer, the term of this patent is extended or adjusted under 35 U.S.C. 154(b) by 56 days.

(21) Appl. No.: 10/591,095

(22) PCT Filed: Mar. 1, 2005

(86) PCT No.: PCT/EP2005/050874

§ 371 (c)(1),
(2), (4) Date: Sep. 20, 2006

(87) PCT Pub. No.: WO2005/083094

PCT Pub. Date: Sep. 9, 2005

(65) Prior Publication Data

US 2007/0136894 A1    Jun. 14, 2007

Related U.S. Application Data

(60) Provisional application No. 60/550,918, filed on Mar. 5, 2004.

(30) Foreign Application Priority Data

Mar. 1, 2004  (EP) .................................. 04100814

(51) Int. Cl.
*C12N 15/82* (2006.01)
*A01H 5/00* (2006.01)

(52) U.S. Cl. .................. 800/290; 800/298; 800/320; 800/320.1; 800/320.2; 800/320.3; 435/320.1

(58) Field of Classification Search .................. None
See application file for complete search history.

(56) References Cited

U.S. PATENT DOCUMENTS 6,329,567 B1 * 12/2001 Jofuku et al. ............... 800/260
2003/0233670 A1 * 12/2003 Edgerton et al. ............ 800/278

FOREIGN PATENT DOCUMENTS

EP    1 033 405 A2    9/2000
WO    WO-02/081623 A2    10/2002
WO    WO 03/027299    *    4/2003
WO    WO-03/027299 A2    4/2003

OTHER PUBLICATIONS

Yamaguchi et al. Control of in vitro organogenesis by cyclin dependent kinase activities in plants. Proc Natl Acad Sci U S A. Jun. 24, 2003;100(13):8019-23. Epub Jun. 10, 2003.*
Fabian-Marwedel et al. The rice cyclin dependent kinase-activating kinase R2 regulates S-phase progression. Plant Cell. Jan. 2002;14(1):197-210.*
Fabian-Marwedel T. et al. The rice cyclin-dependent kinase-activating kinase R2 regulates S phase progression. Plant Cell. Jan. 2002;14(1):197-210.*
Joubes J. et al. CDK-related protein kinases in plants. Plant Mol Biol. Aug. 2000;43(5-6):607-20. Review.*
Komari T et al. Advances in cereal gene transfer. Curr Opin Plant Biol. Apr. 1998;1(2):161-5. Review.*
Hata S. GenBank Accession No. X58194. O. sativa mRNA for cdc2+/CDC28-related protein kinase. Apr. 18, 2005. Sequence alignment with SEQ ID No. 1.*
Cornejo M. et al. Activity of a maize ubiquitin promoter in transgenic rice. Plant Mol Biol. Nov. 1993;23(3):567-81.*
de Pater B.S. et al. The promoter of the rice gene GOS2 is active in various different monocot tissues and binds rice nuclear factor ASF-1. Plant J. Nov. 1992;2(6):837-44.*
Genbank Accession No. P29620, Nov. 25, 2008.*
Fabian-Marwedel, T. et al., "The Rice Cyclin-Dependent Kinase-Activating Kinase R2 Regulates S-Phase Progression," *The Plant Cell*, Jan. 2002, pp. 197-210, vol. 14.
Shimotohno, A. et al., "Differential phosphorylation activities of CDK-activating kinases in *Arabidopsis thaliana*," *FEBS Letters*, (2003), pp. 69-74, vol. 534.
Yamaguchi, M. et al., "Control of in vitro organogenesis by cyclin-dependent kinase activities in plants," Proc Nati Acad Sci USA, Jun. 24, 2003, pp. 8019-8023, vol. 100, No. 13.

* cited by examiner

*Primary Examiner*—Cynthia Collins
(74) *Attorney, Agent, or Firm*—Connolly Bove Lodge & Hutz LLP

(57) ABSTRACT

The present invention concerns a method for increasing plant yield, particularly seed yield, comprising introducing into a plant a nucleic acid encoding a CDKD or a functional variant thereof. The invention also provides transgenic plants produced by the methods of the invention and provides constructs useful in methods of the invention.

20 Claims, 4 Drawing Sheets

SEQ ID NO: 1: CDKD;1 *Arabidopsis thaliana* atggaacagccgaagaaagttgctgataggtatctaaagcgagaggttcttggtcaaggt
acttatggagtcgtcttcaaagctactgatacaaagaatggagaaactgtagcgatcaag
aaaataagacttggtaaagagaagaaggtgtgaatgtaacagctcttagagaaatcaaa
ttacttaaagagcttaagcatccacatataattgagttgattgatgcgtttcctcacaag
gagaatttgcacatcgtgtttgagttcatggagactgatctcgaagcagttatccgagat
cgtaatctctatctttcgcctggtgatgtcaaatcttacctccaaatgatattgaaggt
cttgaatattgccatggcaaatgggttctgcacagagatatgaagccaaacaacttgtt
ataggacccaatggacagctgaaacttgcagattttgggttagcacgtatatttggtagc
ccaggtcgtaagtttacccaccaggtgtttgctagatggtatagagcacctgaacttttg
tttggtgcaaaacaatatgatggtgcagttgatgtttgggctgctggctgcatttttgct
gaacttctattacgcagaccatttcttcagggaaacagtgatattgatcaattaagcaaa
atctttgctgcctttgggactccaaaagcagatcagtggcctgacatgatctgccttcct
gattatgtagagtatcaatttgtccctgctccttctttacgttctttactcccaacggtt
agtgaggatgctttagatttgttgtcaaagatgttcacctatgaccccaagtctagaata
tcgattcagcaggctctaaaacacaggtacttcacatctgcaccttcacctactgaccct
ttaaagctcccaagaccagtttccaagcaagatgctaagtcatctgatagtaaacttgaa
gccattaaagtgctgtcaccagcacataagtttagaagagtgatgcctgaccgaggaaag
tctggtaatggtttcaaggaccagagtgttgatgtcatgagacaagctagccatgatgga
caagcaccaatgtctttagatttcaccatcttagctgagcggccaccaaaccgaccaacc
atcaccagtgcagatagatctcatctgaagaggaaacttgatctcgagttcctataggat
atcgcgtaacaggcttcttcttgacgtcgttcttcaggttcctatagcctatagga

SEQ ID NO: 2: CDKD;1 *Arabidopsis thaliana*

MEQPKKVADRYLKREVLGQGTYGVVFKATDTKNGETVAIKKIRLGKEKEGVNVTALREIK
LLKELKHPHIIELIDAFPHKENLHIVFEFMETDLEAVIRDRNLYLSPGDVKSYLQMILKG
LEYCHGKWVLHRDMKPNNLLIGPNGQLKLADFGLARIFGSPGRKFTHQVFARWYRAPELL
FGAKQYDGAVDVWAAGCIFAELLLRRPFLQGNSDIDQLSKIFAAFGTPKADQWPDMICLP
DYVEYQFVPAPSLRSLLPTVSEDALDLLSKMFTYDPKSRISIQQALKHRYFTSAPSPTDP
LKLPRPVSKQDAKSSDSKLEAIKVLSPAHKFRRVMPDRGKSGNGFKDQSVDVMRQASHDG
QAPMSLDFTILAERPPNRPTITSADRSHLKRKLDLEFL

FIGURE 3

**SEQ ID NO: 3: G0S2 promoter *Oryza sativa***
```
aatccgaaaagtttctgcaccgttttcaccccctaactaacaatatagggaacgtgtgc
taaatataaaatgagaccttatatatgtagcgctgataactagaactatgcaagaaaaa
ctcatccacctactttagtggcaatcgggctaaataaaaagagtcgctacactagttt
cgttttccttagtaattaagtgggaaaatgaaatcattattgcttagaatatacgttca
catctctgtcatgaagttaaattattcgaggtagccataattgtcatcaaactcttctt
gaataaaaaatctttctagctgaactcaatgggtaaagagagagattttttttaaaaa
aatagaatgaagatattctgaacgtattggcaaagatttaaacatataattatataatt
ttatagtttgtgcattcgtcatatcgcacatcattaaggacatgtcttactccatccca
atttttatttagtaattaaagacaattgacttattttattatttatctttttttcgatt
agatgcaaggtacttacgcacacactttgtgctcatgtgcatgtgtgagtgcacctcct
caatacacgttcaactagcaacacatctctaatatcactcgcctatttaatacatttag
gtagcaatatctgaattcaagcactccaccatccagaccacttttaataatatctaa
aatacaaaaaataattttacagaatagcatgaaaagtatgaaacgaactatttaggttt
ttcacatacaaaaaaaaaagaattttgctcgtgcgcgagcgccaatctcccatattgg
gcacacaggcaacaacagagtggctgcccacagaacaacccacaaaaaacgatgatcta
acggaggacagcaagtccgcaacaaccttttaacagcaggctttgcggccaggagagag
gaggagaggcaaagaaaaccaagcatcctcctcctcccatctataaattcctcccccct
tttcccctctctatataggaggcatccaagccaagaagagggagagcaccaaggacacg
cgactagcagaagccgagcgaccgccttcttcgatccatatcttccggtcgagttcttg
gtcgatctcttccctcctccacctcctcctcacagggtatgtgcccttcggttgttctt
ggatttattgttctaggttgtgtagtacgggcgttgatgttaggaaaggggatctgtat
ctgtgatgattcctgttcttggatttgggatagaggggttcttgatgttgcatgttatc
ggttcggtttgattagtagtatggttttcaatcgtctggagagctctatggaaatgaaa
tggtttagggtacggaatcttgcgattttgtgagtaccttttgtttgaggtaaaatcag
agcaccggtgattttgcttggtgtaataaaagtacggttgtttggtcctcgattctggt
agtgatgcttctcgatttgacgaagctatcctttgtttattccctattgaacaaaaata
atccaactttgaagacggtcccgttgatgagattgaatgattgattcttaagcctgtcc
aaaatttcgcagctggcttgtttagatacagtagtccccatcacgaaattcatggaaac
agttataatcctcaggaacaggggattccctgttcttccgatttgctttagtcccagaa
ttttttttcccaaatatcttaaaaagtcactttctggttcagttcaatgaattgattgc
tacaaataatgcttttatagcgttatcctagctgtagttcagttaataggtaataccc
tatagtttagtcaggagaagaacttatccgatttctgatctccattttaattatatga
aatgaactgtagcataagcagtattcatttggattattttttttattagctctcacccc
ttcattattctgagctgaaagtctggcatgaactgtcctcaattttgttttcaaattca
catcgattatctatgcattatcctcttgtatctacctgtagaagtttcttttttggttat
tccttgactgcttgattacagaaagaaatttatgaagctgtaatcgggatagttatact
gcttgttcttatgattcatttcctttgtgcagttcttggtgtagcttgccactttcacc
agcaaagttc
```

SEQ ID NO: 4: prm2676 sense, start codon in bold, AttB1 site in italic
*GGGGACAAGTTTGTACAAAAAAGCAGGCTTCACA* ATGGAACAGCCGAAGAAAG

SEQ ID NO: 5: prm2677 reverse, complementary, stop codon in bold, AttB2 site in italic
*GGGGACCACTTTGTACAAGAAAGCTGGGT*CCTATAGGAACTCGAGATCAAGTT

PLANTS HAVING INCREASED YIELD AND METHOD FOR MAKING THE SAME

RELATED APPLICATIONS

This application is a national stage application (under 35 U.S.C. §371) of PCT/EP2005/050874 filed Mar. 1, 2005, which claims benefit of European application 04100814.5 filed Mar. 1, 2004 and U.S. provisional application 60/550,918 filed Mar. 5, 2004.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_List_14546_00001_US. The size of the text file is 11 KB, and the text file was created on Sep. 11, 2009.

The present invention relates generally to the field of molecular biology and concerns a method for increasing plant yield. More specifically, the present invention concerns a method for increasing plant yield, particularly seed yield, by introducing into a plant a nucleic acid encoding a D-type Cyclin-Dependent Kinase (CDKD). The present invention also concerns plants produced by the methods according to the invention, which plants have increased yield relative to corresponding wild type plants. The invention also concerns constructs useful in the methods of the invention.

The ever-increasing world population and the dwindling supply of arable land available for agriculture fuel research towards improving the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits. A trait of particular economic interest is yield. Yield is normally defined as the measurable produce of economic value from a crop. This may be defined in terms of quantity and/or quality. Yield is directly dependent on several factors, for example, the number and size of the organs, plant architecture (for example, the number of branches), seed production and more. Root development, nutrient uptake and stress tolerance are also important factors in determining yield. Crop yield may be increased by optimizing one of the abovementioned factors, which may be done by modifying the inherent growth mechanisms of a plant.

The inherent growth mechanisms of a plant reside in a highly ordered sequence of events collectively known as the 'cell cycle'. Progression through the cell cycle is fundamental to the growth and development of all multicellular organisms and is crucial to cell proliferation. The major components of the cell cycle are highly conserved in yeast, mammals, and plants. The cell cycle is typically divided into the following sequential phases: G0-G1-S-G2-M. DNA replication or synthesis generally takes place during the S phase ("S" is for DNA synthesis) and mitotic segregation of the chromosomes occurs during the M phase (the "M" is for mitosis), with intervening gap phases, G1 (during which cells grow before DNA replication) and G2 (a period after DNA replication during which the cell prepares for division). Cell division is completed after cytokinesis, the last step of the M phase. Cells that have exited the cell cycle and that have become quiescent are said to be in the G0 phase. Cells in this phase can be stimulated to renter the cell cycle at the G1 phase. The "G" in G1, G2 and G0 stands for "gap". Completion of the cell cycle process allows each daughter cell during cell division to receive a full copy of the parental genome.

Cell division is controlled by two principal cell cycle events, namely initiation of DNA synthesis and initiation of mitosis. Each transition to each of these key events is controlled by a checkpoint represented by specific protein complexes (involved in DNA replication and division). The expression of genes necessary for DNA synthesis at the G1/S boundary is regulated by the E2F family of transcription factors in mammals and plant cells (La Thangue, 1994; Muller et al., 2001; De Veylder et al., 2002). Entry into the cell cycle is regulated/triggered by an E2F/Rb complex that integrates signals and allows activation of transcription of cell cycle genes. The transition between the different phases of the cell cycle, and therefore progression through the cell cycle, is driven by the formation and activation of different heterodimeric serine/threonine protein kinases, generally referred to as cyclin-dependent kinases (CDKs). A prerequisite for activity of these kinases is the physical association with a specific cyclin, the timing of activation being largely dependent upon cyclin expression. Cyclin binding induces conformational changes in the N-terminal lobe of the associating CDK and contributes to the localisation and substrate specificity of the complex. Monomeric CDKs are activated when they are associated with cyclins and thus have a kinase activity. Cyclin protein levels fluctuate in the cell cycle and therefore represent a major factor in determining timing of CDK activation. The periodic activation of these complexes containing cyclins and CDK during cell cycle mediates the temporal regulation of cell-cycle transitions (checkpoints). Other factors regulating CDK activity include CDK inhibitors (CKIs or ICKs, KIPs, CIPs, INKs), CDK activating kinases (CAK), CDK phosphatasea (Cdc25) and CDK subunits (CKS) (Mironov et al. 1999; Reed 1996).

In plants, two major classes of CDKs, known as A-type and B-type CDKs, have been studied to date. The A-type CDKs regulate both the G1-to-S and G2-to-M transitions, whereas the B-type CDKs seem only to control the G2-to-M checkpoint (Hemerly et al., 1995; Magyar et al., 1997; Porceddu et al., 2001). In addition, the presence of C-type CDKs and CDK-activating kinases (CAKs) has been reported (Magyar et al., 1997; Umeda et al., 1998; Joubès et al., 2001). Vandepoele et al., 2002, identified four CAKs by a homology-based annotation method. These CAKs were three D type CAKs (Arath;CDKM;1, Arath;CDKD;2 and Arath;CDKD;3); and one F-type CAK (Arath;CDKF;1).

Yamaguchi et al. (PNAS Vol. 100 (13) 8019-8023, 2003) describe the overexpression of rice R2 cDNA (which encodes a CAK) in tobacco leaf explants. They reported that transient expression of R2 during the first 7 days of culture triggered callus formation in the absence of cytokinin. Yamaguchi et al. also examined the control of in vitro organogenesis by CDK.

Fabian-Marwedel et al, (The Plant Cell, Vol. 14, 197-210, 2002) report that the rice CAK, R2, regulates S-phase progression and overall growth rate in suspension cells.

The ability to influence the cell cycle of a plant, and to thereby modify various growth characteristics of a plant, would have applications in areas such as crop enhancement, plant breeding, in the production of ornamental plants, aboriculture, horticulture, forestry, the production of algae for use in bioreactors (for the biotechnological production of substances such as pharmaceuticals, antibodies, or vaccines, or for the bioconversion of organic waste) and other such areas.

It has now been found that introduction into a plant of a CDKD-encoding nucleic acid gives plants having increased yield relative to corresponding wild type plants. Therefore according to one embodiment of the present invention there is provided a method for increasing yield in a plant, comprising introducing into a plant a nucleic acid encoding a CDKD.

The term "increased yield" as defined herein is taken to mean an increase in any one or more of the following, each relative to corresponding wild type plants: (i) increased biomass (weight) of one or more parts of a plant, particularly aboveground (harvestable) parts, increased root biomass or increased biomass of any other harvestable part; (ii) increased seed yield, which may result from an increase in the biomass of the seed (seed weight) and which may be an increase in the seed weight per plant or on an individual seed basis, and which increase in seed weight may be due to altered seed dimensions, such as seed length and/or seed width and/or seed area; (iii) increased number of (filled) seeds; (iv) increased seed size, which may also influence the composition of seeds; (v) increased seed volume, which may also influence the composition of seeds; (vi) increased harvest index, which is expressed as a ratio of the yield of harvestable parts, such as seeds, over the total biomass; and (vii) increased thousand kernel weight (TKW), which is extrapolated from the number of filled seeds counted and their total weight. An increased TKW may result from an increased seed size and/or seed density.

According to a preferred embodiment of the invention, the increase in yield encompasses an increase in yield on a seed level as defined in any one or more of (ii) to (vii) above.

Taking corn as an example, a yield increase may be manifested as one or more of the following: increase in the number of plants per hectare or acre, an increase in the number of ears per plant, an increase in the number of rows, number of kernels per row, kernel weight, thousand kernel weight, ear length/diameter, among others. Taking rice as an example, a yield increase may be manifested by an increase in one or more of the following: number of plants per hectare or acre, number of panicles per plant, number of spikelets per panicle, number of flowers per panicle, increase in the seed filling rate, increase in thousand kernel weight, among others. An increase in yield may also result in modified architecture, or may occur as a result of modified architecture.

According to a preferred feature, performance of the methods of the invention result in plants having increased yield which is manifested by at least one of: increased aboveground area, increased TKW, increased number of filled seeds, increased seed weight and increased harvest index, each relative to control or corresponding wild-type plants.

Performance of the methods of the invention advantageously leads to increased yield in any plant.

The term "plant" as used herein encompasses whole plants, ancestors and progeny of the plants and plant parts, including seeds, shoots, stems, leaves, roots (including tubers), and plant cells, tissues and organs, wherein each of the aforementioned comprise the gene of interest. The term "plant" also encompasses embryos, meristematic regions, gametophytes, sporophytes, pollen, and microspores, again wherein each of the aforementioned comprise the gene of interest. The term plant, as defined herein, does not include suspension cultures and callus tissue.

The methods of the invention may be performed on any plant, particularly all plants which belong to, the superfamily Viridiplantae, in particular monocotyledonous and dicotyledonous plants including fodder or forage legumes, ornamental plants, food crops, trees or shrubs selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp., *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp., *Camellia sinensis*, *Canna indica*, *Capsicum* spp., *Cassia* spp., *Centroema pubescens*, *Chaenomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Diheteropogon amplectens*, *Dioclea* spp, *Dolichos* spp., *Dorycnium rectum*, *Echinochloa pyramidalis*, *Ehrartia* spp., *Eleusine coracana*, *Eragrestis* spp., *Erythrina* spp., *Eucalyptus* spp., *Euclea schimperi*, *Eulalia villosa*, *Fagopyrum* spp., *Feijoa sellowiana*, *Fragaria* spp., *Flemingia* spp, *Freycinetia banksii*, *Geranium thunbergii*, *Ginkgo biloba*, *Glycine javanica*, *Gliricidia* spp., *Gossypium hirsutum*, *Grevillea* spp., *Guibourtia coleosperma*, *Hedysarum* spp., *Hemarthia altissima*, *Heteropogon contortus*, *Hordeum vulgare*, *Hyparrhenia rufa*, *Hypericum erectum*, *Hyperthelia dissoluta*, *Indigo incarnata*, *Iris* spp., *Leptarrhena pyrolifolia*, *Lespediza* spp., *Lettuca* spp., *Leucaena leucocephala*, *Loudetia simplex*, *Lotonus bainesii*, *Lotus* spp., *Macrotyloma axillare*, *Malus* spp., *Manihot esculenta*, *Medicago sativa*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativum*, *Podocarpus totara*, *Pogonarthria fleckii*, *Pogonarthria squarrosa*, *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys verticillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp., *Taxodium distichum*, *Themeda triandra*, *Trifolium* spp., *Triticum* spp., *Tsuga heterophylla*, *Vaccinium* spp., *Vicia* Spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, strawberry, sugar beet, sugar cane, sunflower, tomato, squash, tea and algae, amongst others. According to a preferred embodiment of the present invention, the plant is a crop plant such as soybean, sunflower, canola, alfalfa, rapeseed, cotton, tomato, potato or tobacco. Further preferably, the plant is a monocotyledonous plant, such as sugar cane. More preferably the plant is a cereal, such as rice, maize, wheat, barley, millet, rye, sorghum or oats.

The terms "D-type CDK" or "CDKD" are used interchangeably herein and refer to any amino acid sequence which, when used in the construction of a CDK phylogenetic tree, such as the one depicted in FIG. 1, clusters around or in a group which includes D-type CDKs, but no other CDK types, such as A-, B-, C-, E- or F-type CDKs. Reference herein to a nucleic acid encoding a CDKD is to a nucleic acid encoding a CDKD amino acid as defined above.

A person skilled in the art could readily determine whether any amino acid sequence in question falls within the aforementioned definition using known techniques and software for the making of such a phylogenetic tree, such as a GCG, EBI or CLUSTAL package, using default parameters. Upon construction of such a phylogenetic tree, sequences clustering around or in the D-type CDK group will be considered to fall within the definition of a "D-type CDK". Nucleic acids encoding such sequences will be useful in performing the methods of the invention.

D-type CDKs typically have the ability to phosphorylate and activate CDKs and have also been shown to phosphorylate and activate RNA polymerase II. D-type CDKs may also exhibit one or more and preferably all of the following features: (i) an NXTALRE motif (SEQ ID NO: 6), where X is any amino acid; (ii) a catalytic kinase domain; and (iii) the ability to bind to cyclin H.

A CDKD may easily be distinguished from any other CDK since the motif NXTALRE (SEQ ID NO: 6) is particular to this type of CDK (according to current knowledge). In contrast, according to current knowledge, an A-type CDK will have a PSTAIRE motif (SEQ ID NO: 7); a B-type CDK a P(P/S)T(A/T)(L/M)RE motif (SEQ ID NO: 8); a C-type CDK a PITAIRE motif (SEQ ID NO: 9); an E-type CDK will have an SPTARE motif (SEQ ID NO: 10); and an F-type CDK will have a XSAXRE motif (SEQ ID NO: 11).

A person skilled in the art may readily assay for kinase activity on, for example, purified substrates such as human CAK2 or on the *Arabidopsis thaliana* RNA polymerase II carboxy-terminus. The ability of a CDKD to bind to cyclin H may readily be determined by co-precipitation of CDKD-cyclin H complexes from purified CDKD and cyclin H, or by using a two hybrid assay.

In *Arabidopsis thaliana*, CDKDs are encoded by 3 different genes, CDKD;1, CDKD;2 and CDKD;3, each gene encoding a protein which comprises the motif NXTALRE (SEQ ID NO: 6), wherein X is any amino acid.

Advantageously, the methods of the invention may be performed using any nucleic acid encoding a CDKD as defined hereinabove. Introduction into a plant of a CDKD-encoding nucleic acid gives modulated expression (preferably increased expression) in a plant of such a nucleic acid and/or modulated (preferably increased) activity and/or levels in a plant of a CDKD polypeptide. The activity of a CDKD may be increased by increasing levels of the polypeptide. Alternatively, activity may be increased when there is no change in levels of a CDKD polypeptide, or even when there is a reduction in levels of a CDKD polypeptide. This may occur when the intrinsic properties of the polypeptide are altered, for example, by making mutant versions that are more active than the wild type polypeptide.

The nucleic acid encoding a CDKD is preferably operably linked to a constitutive promoter for overexpression in a plant. The constitutive promoter is preferably a GOS2 promoter, further preferably a GOS2 promoter from rice. It should be clear that the applicability of the present invention is not restricted to use of a CDKD from *Arabidopsis thaliana*, nor to a CDKD represented by SEQ ID NO: 1, nor is the applicability of the invention restricted to expression of a CDKD-encoding nucleic acid when driven by a GOS2 promoter.

According to a preferred aspect of the present invention, enhanced or increased expression of the CDKD nucleic acid is envisaged. Methods for obtaining enhanced or increased expression of genes or gene products are well documented in the art and include, for example, overexpression driven by a strong promoter, the use of transcription enhancers or translation enhancers.

The nucleic acid encoding a CDKD may be derived from any source. The nucleic acid/gene encoding a CDKD may be isolated from a microbial source, such as bacteria, yeast or fungi, or from a plant, algae or animal (including human) source. This nucleic acid may be modified from its native form in composition and/or genomic environment through deliberate human manipulation. The nucleic acid is preferably a homologous nucleic acid, i.e. a nucleic acid obtained from a plant, whether from the same plant species in which it is to be introduced or whether from a different plant species. The nucleic acid may be isolated from a *dicotyledonous* species, preferably from the family Brassicaceae, further preferably from *Arabidopsis thaliana*. More preferably, the CDKD-encoding nucleic acid is isolated from *Arabidopsis thaliana* is a CDKD;1, CDKD;2 or a CDKD;3. Most preferably, the CDKD is CDKD;1 from *Arabidopsis thaliana*, particularly the nucleic acid sequence as represented by SEQ ID NO: 1 and the corresponding amino acid sequence as represented by SEQ ID NO: 2.

Advantageously, the performance of the present invention is not restricted to the use of a CDKD;1 from *Arabidopsis* as represented by SEQ ID NO: 1. The methods according to the present invention may also be practised using functional variants of a CDKD as defined hereinabove or using functional variants of CDKD-encoding nucleic acids. Preferred functional variants are variants of the nucleic acid sequence represented by SEQ ID NO: 1 or functional variants of the amino acid sequence represented by SEQ ID NO: 2.

The term "functional variant" as defined herein is a variant which falls under the definition of a CDKD as hereinbefore defined. Preferably, the functional variant also has the ability to phosphorylate and activate CDKs and phosphorylate and activate RNA polymerase II. Preferably, the D-type CDK functional variant also exhibits one or more and preferably all of the following features: (i) an NXTALRE motif (SEQ ID NO: 6), where X is any amino acid; (ii) a catalytic kinase domain; and (iii) the ability to bind to cyclin H. A person skilled in the art may also readily determine whether a particular variant is functional (in the sense of whether it is able to increase plant yield) by simply substituting the sequence described in the Examples section below with the variant to be tested for function.

Suitable variant nucleic acid and amino acid sequences useful in practising the method according to the invention, include:

(i) Functional portions of a CDKD-encoding nucleic acid;
(ii) Sequences capable of hybridising to a CDKD-encoding nucleic acid;
(iii) Alternative splice variants of a CDKD-encoding nucleic acid;
(iv) Allelic variants of a CDKD-encoding nucleic acid; and
(v) Homologues, derivatives and active fragments of a CDKD amino acid.

Each of the aforementioned variants is a functional variant, as defined hereinbefore.

It will be apparent to a person skilled in the art that the use of the full-length CDKD-encoding DNA sequence would not be a prerequisite to carrying out the methods according to the invention. The methods according to the invention may advantageously be practised using functional portions of a CDKD-encoding DNA/nucleic acid, preferably functional portions of a nucleic acid sequence as represented by SEQ ID NO: 1 A functional portion is a CDKD-encoding nucleic acid falling under the definition of a functional variant as defined hereinabove. A portion may be prepared, for example, by making one or more deletions to a CDKD-encoding nucleic acid, such as the nucleic acid sequence of SEQ ID NO: 1, using techniques well known in the art.

Therefore according to the invention, there is provided, a method for increasing plant yield, in particular seed yield, comprising introducing into a plant a portion of a CDKD-encoding nucleic acid.

Another variant is a sequence capable of hybridising to a CDKD-encoding nucleic acid. Such hybridising sequences are those falling under the definition of functional variants as defined hereinabove. Particularly preferred are sequences capable of hybridising to a CDKD-encoding nucleic acid under stringent conditions, especially to a CDKD-encoding nucleic acid as represented by SEQ ID NO: 1.

The term "hybridisation" as defined herein is a process wherein substantially homologous complementary nucleotide sequences anneal to each other. The hybridization process can occur entirely in solution, i.e. both complementary nucleic acids are in solution. Tools in molecular biology relying on such a process include the polymerase chain reaction (PCR; and all methods based thereon), subtractive hybridisation, random primer extension, nuclease S1 mapping, primer extension, reverse transcription, cDNA synthesis, differential display of RNAs, and DNA sequence determination. The hybridisation process can also occur with one of the complementary nucleic acids immobilised to a matrix such as magnetic beads, Sepharose beads or any other resin. Tools in molecular biology relying on such a process include the isolation of poly ($A^+$) mRNA. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). Tools in molecular biology relying on such a process include RNA and DNA gel blot analysis, colony hybridisation, plaque hybridisation, in situ hybridisation and microarray hybridisation. In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration and hybridisation buffer composition. Hybridisation preferably occurs under stringent conditions. Stringent conditions are those that (1) employ low ionic strength and high temperature for washing, for example, 0.5M sodium phosphate buffer pH 7.2, 1 mM EDTA pH 8.0 in 7% SDS at either 65° C. or 55° C., or (2) employ during hybridization a denaturing agent such as formamide, for example, 50% (vol/vol) formamide with 0.1% bovine serum albumin, 0.1% Ficoll, 0.1% polyvinylpolypyrrolidone, 0.05 M sodium phosphate buffer at pH 6.5 with 0.75 M NaCl, 0.075 M sodium citrate at 42° C. A specific example includes the use of 50% formamide, 5×SSC (0.75 M NaCl, 0.075 M sodium citrate), 50 mM sodium phosphate (pH 6.8), 0.1% sodium pyrophosphate, 5× Denhard's solution, sonicated salmon sperm DNA (50 mm/ml), 0.1% SDS and 10% dextran sulfate at 55° C., with washes at 55° C. in 0.2×SSC and 0.1% SDS. A skilled person can readily determine and vary the stringency conditions appropriately to obtain a clear and detectable hybridization signal.

Therefore according to the invention, there is provided, a method for increasing plant yield, comprising introducing into a plant a sequence capable of hybridising, preferably under stringent conditions, to a CDKD-encoding nucleic acid.

Another variant useful in the methods of the invention is an alternative splice variant of a CDKD-encoding nucleic acid. Suitable splice variants are those falling under the definition of a functional variant as defined hereinabove. The term "alternative splice variant" as used herein encompasses variants of a nucleic acid in which selected introns and/or exons have been excised, replaced or added. Such variants will be ones in which the biological activity of the protein remains unaffected, which can be achieved by selectively retaining functional segments of the protein. Such splice variants may be found in nature or may be manmade. Methods for making such splice variants are well known in the art. Splice variants of SEQ ID NO: 1 are particularly preferred for use in the methods according to the invention.

Therefore, the invention also provides a method for increasing plant yield, comprising introducing into a plant an alternative splice variant of a CDKD-encoding nucleic acid.

Another variant useful in the methods of the invention is an allelic variant of a CDKD-encoding nucleic acid. Suitable allelic variants are those falling under the definition of a functional variant as defined hereinabove. Allelic variants exist in nature and encompassed within the methods of the present invention is the use of these natural alleles. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms. Allelic variants of SEQ ID NO: 1 are particularly preferred for use in the methods according to the invention.

Therefore, the invention also provides a method for increasing plant yield, comprising introducing into a plant an allelic variant of a CDKD-encoding nucleic acid.

Further advantageously, the methods according to the present invention may also be practised using homologues, derivatives or active fragments of a CDKD. Nucleic acids encoding homologues, derivatives or active fragments of an amino acid, such as the one represented by SEQ ID NO: 2, may readily be determined using routine techniques well known to persons skilled in the art. Such nucleic acids suitable for use in the methods of the invention may readily be determined as described hereinbefore.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company).

The homologues useful in the methods according to the invention have in increasing order of preference at least 50%, 55%, 60%, 65%, 70%, 75%, 80%, 85%, 90%, 95% sequence identity to the amino acid sequence as represented by SEQ ID NO: 2. CDKDs show about 65% identity to each other and show less than 40% identity to other CDKs. Therefore a homologue having at least 50% identity to the CDK as represented by SEQ ID NO: 2 will not encompass any other CDK other than a D-type CDK.

Also encompassed by the term "homologues" are two special forms of homology, which include orthologous sequences and paralogous sequences, which encompass evolutionary concepts used to describe ancestral relationships of genes. The term "paralogous" relates to gene-duplications within the genome of a species leading to paralogous genes. The term "orthologous" relates to homologous genes in different organisms due to ancestral relationship.

Othologues in, for example, monocot plant species may easily be found by performing a so-called reciprocal blast search. This may be done by a first blast involving blasting the sequence in question (for example, SEQ ID NO: 1 or SEQ ID NO: 2) against any sequence database, such as the publicly available NCBI database which may be found at: http://www.ncbi.nim.nih.gov. If orthologues in rice were sought, the sequence in question would be blasted against, for example, the 28,469 full-length cDNA clones from *Oryza sativa* Nipponbare available at NCBI. BLASTn may be used when starting from nucleotides or TBLASTX when starting from the protein, with standard default values (expectation 10, alignment 50). The blast results may be filtered. The full-length sequences of either the filtered results or the non-filtered results are then blasted back (second blast) against the sequence in question (SEQ ID NO: 1 or 2). The results of the first and second blasts are then compared. In the case of large families, ClustalW is used followed by a neighbour joining tree to help visualize the clustering.

A homologue may be in the form of a "substitutional variant" of a protein, i.e. where at least one residue in an amino acid sequence has been removed and a different residue inserted in its place. Amino acid substitutions are typically of single residues, but may be clustered depending upon functional constraints placed upon the polypeptide; insertions will usually be of the order of about 1 to 10 amino acid residues, and deletions will range from about 1 to 20 residues. Preferably, amino acid substitutions comprise conservative amino acid substitutions.

A homologue may also be in the form of an "insertional variant" of a protein, i.e. where one or more amino acid residues are introduced into a predetermined site in a protein. Insertions may comprise amino-terminal and/or carboxy-terminal fusions as well as intra-sequence insertions of single or multiple amino acids. Generally, insertions within the amino acid sequence will be smaller than amino- or carboxy-terminal fusions, of the order of about 1 to 10 residues. Examples of amino- or carboxy-terminal fusion proteins or peptides include the binding domain or activation domain of a transcriptional activator as used in the yeast two-hybrid system phage coat proteins, (histidine)6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

Homologues in the form of "deletion variants" of a protein are characterised by the removal of one or more amino acids from a protein.

Amino acid variants of a protein may readily be made using peptide synthetic techniques well known in the art, such as solid phase peptide synthesis and the like, or by recombinant DNA manipulations. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

"Derivatives" include peptides, oligopeptides, polypeptides, proteins and enzymes which may comprise substitutions, deletions or additions of naturally and non-naturally occurring amino acid residues compared to the amino acid sequence of a naturally-occurring form of the protein, for example, as presented in SEQ ID NO: 2. "Derivatives" of a protein encompass peptides, oligopeptides, polypeptides, proteins and enzymes which may comprise naturally occurring altered, glycosylated, acylated or non-naturally occurring amino acid residues compared to the amino acid sequence of a naturally-occurring form of the polypeptide. A derivative may also comprise one or more non-amino acid substituents compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein.

"Active fragments" of a CDKD protein encompasses sufficient amino acid residues to cluster around or in the D-type CDK group upon construction of a phylogenetic tree, such as the one shown in FIG. 1. When using fragments in such a phylogenetic tree, like should be compared with like, meaning that corresponding fragments of the other CDKs should be used to make the tree.

Methods for the search and identification of CDKD homologues would be well within the realm of a person skilled in the art. Methods for the alignment of sequences for comparison are well known in the art, such methods include GAP, BESTFIT, BLAST, FASTA and TFASTA. GAP uses the algorithm of Needleman and Wunsch (J. Mol. Biol. 48: 443-453, 1970) to find the alignment of two complete sequences that maximises the number of matches and minimises the number of gaps. The BLAST algorithm calculates percent sequence identity and performs a statistical analysis of the similarity between the two sequences. The software for performing BLAST analysis is publicly available through the National Centre for Biotechnology Information. Homologues suitable for use in the methods of the invention, i.e. those having at least 50% sequence identity to the amino acid sequence represented by SEQ ID NO: 2, may be identified by taking full length CDK protein sequences and aligning them using the ClustalX1.81 software using default parameters. A distance matrix may then be calculated from this alignment using BOXSHADE software, again using default parameters. Both software programs are publicly available.

Therefore, the invention also provides a method for increasing plant yield, comprising introducing into a plant a nucleic acid encoding a homologue, derivative or active fragment of a CDKD, such as a CDKD represented by SEQ ID NO: 2, which homologue, derivative or active fragment has in increasing order of preference at least 50%, 55%, 60%, 65%, 70%, 75%, 80%, 85%, 90%, 95% sequence identity to an amino acid sequence as represented by SEQ ID NO: 2.

The invention also provides genetic constructs and vectors to facilitate introduction and/or expression of the nucleotide sequences useful in the methods according to the invention.

Therefore, there is provided a gene construct comprising:
(i) a CDKD-encoding nucleic acid, preferably as represented by SEQ ID NO: 1 or a functional variant thereof (as defined hereinabove);

(ii) one or more control sequences capable of driving expression of the nucleic acid sequence of (i); and optionally (iii) a transcription termination sequence.

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells.

Plants are transformed with a vector comprising the sequence of interest (i.e., a nucleic acid as represented by SEQ ID NO: 1 or a functional variant thereof (as defined hereinabove)). The sequence of interest is operably linked to one or more control sequences (at least to a promoter). The terms "regulatory element", "control sequence" and "promoter" are all used interchangeably herein and are to be taken in a broad context to refer to regulatory nucleic acid sequences capable of effecting expression of the sequences to which they are ligated. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative which confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest.

Preferably, the nucleic acid encoding a CDKD or a functional variant thereof is operably linked to a constitutive promoter. The term "constitutive promoter" as defined herein refers to a promoter that is expressed predominantly in at least one tissue or organ and predominantly at any stage in the life cycle of a plant. Preferably, the constitutive promoter is expressed predominantly throughout the plant. Preferably, the constitutive promoter is the GOS2 promoter from rice.

Examples of other constitutive promoters suitable for use in the methods of the invention are listed in Table A below.

TABLE A

Examples of constitutive promoters for use in performance of the invention

| GENE SOURCE | EXPRESSION PATTERN | REFERENCE |
|---|---|---|
| Actin | Constitutive | McElroy et al, Plant Cell, 2: 163-171, 1990 |
| CAMV 35S | Constitutive | Odell et al, Nature, 313: 810-812, 1985 |
| CaMV 19S | Constitutive | Nilsson et al., Physiol. Plant. 100: 456-462, 1997 |
| GOS2 | Constitutive | de Pater et al, Plant J Nov; 2(6): 837-44, 1992 |
| Ubiquitin | Constitutive | Christensen et al, Plant Mol. Biol. 18: 675-689, 1992 |
| rice cyclophilin | constitutive | Buchholz et al, Plant Mol Biol. 25(5): 837-43, 1994 |

TABLE A-continued

Examples of constitutive promoters for use in performance of the invention

| GENE SOURCE | EXPRESSION PATTERN | REFERENCE |
|---|---|---|
| maize H3 histone | Constitutive | Lepetit et al, Mol. Gen. Genet. 231: 276-285, 1992 |
| actin 2 | Constitutive | An et al, Plant J. 10(1); 107-121, 1996 |

Optionally, one or more terminator sequences may also be used in the construct introduced into a plant. The term "terminator" encompasses a control sequence which is a DNA sequence at the end of a transcriptional unit which signals 3' processing and polyadenylation of a primary transcript and termination of transcription. Additional regulatory elements may include transcriptional as well as translational enhancers. Those skilled in the art will be aware of terminator and enhancer sequences which may be suitable for use in performing the invention. Such sequences would be known or may readily be obtained by a person skilled in the art.

The genetic constructs of the invention may further include an origin of replication sequence which is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

The genetic construct may optionally comprise a selectable marker gene. As used herein, the term "selectable marker gene" includes any gene which confers a phenotype on a cell in which it is expressed to facilitate the identification and/or selection of cells which are transfected or transformed with a nucleic acid construct of the invention. Suitable markers may be selected from markers that confer antibiotic or herbicide resistance. Cells containing the recombinant DNA will thus be able to survive in the presence of antibiotic or herbicide concentrations that kill untransformed cells. Examples of selectable marker genes include the bar gene which provides resistance to the herbicide Basta; the npt gene which confers resistance to the antibiotic kanamycin; the hpt gene which confers hygromycin resistance. Visual markers, such as the Green Fluorescent Protein (GFP, Haseloff et al., 1997), β-glucuronidase (GUS) or luciferase may also be used as selectable markers. Further examples of suitable selectable marker genes include the ampicillin resistance (Ampr), tetracycline resistance gene (Tcr), bacterial kanamycin resistance gene (Kanr), phosphinothricin resistance gene, neomycin phosphotransferase gene (nptII), hygromycin resistance gene, gene, and the chloramphenicol acetyltransferase (CAT) gene, amongst others.

The present invention also encompasses plants obtainable by the methods according to the present invention. The present invention therefore provides plants obtainable by the method according to the present invention, which plants have increased yield and which plants have altered CDKD protein activity and/or levels and/or altered expression of a nucleic acid encoding a CDKD protein relative to corresponding wild-type plants.

The invention also provides a method for the production of transgenic plants having increased yield, comprising introduction and expression in a plant of a CDKD-encoding nucleic acid or a functional variant thereof (as defined hereinabove).

More specifically, the present invention provides a method for the production of transgenic plants having increased yield, which method comprises:

(i) introducing into a plant or plant cell a CDKD-encoding nucleic acid or a functional variant thereof (as defined hereinabove);

(ii) cultivating the plant cell under conditions promoting regeneration and mature plant growth.

The nucleic acid may be introduced directly into a plant cell or into the plant itself (including introduction into a tissue, organ or any other part of a plant). According to a preferred feature of the present invention, the nucleic acid is preferably introduced into a plant by transformation.

The term "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

Transformation of plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., 1882, Nature 296, 72-74; Negrutiu I. et al., June 1987, Plant Mol. Biol. 8, 363-373); electroporation of protoplasts (Shillito R. D. et al., 1985 Bio/Technol 3, 1099-1102); microinjection into plant material (Crossway A. et al., 1986, Mol. Gen Genet 202, 179-185); DNA or RNA-coated particle bombardment (Klein T. M. et al., 1987, Nature 327, 70) infection with (non-integrative) viruses and the like. Transgenic rice plants expressing a CDKD-encoding nucleic acid are preferably produced via *Agrobacterium*-mediated transformation using any of the well known methods for rice transformation, such as described in any of the following: published European patent application EP 1198985 A1, Aldemita and Hodges (Planta, 199, 612-617, 1996); Chan et al. (Plant Mol. Biol. 22 (3) 491-506, 1993), Hiei et al. (Plant J. 6 (2) 271-282, 1994), which disclosures are incorporated by reference herein as if fully set forth. In the case of corn transformation, the preferred method is as described in either Ishida et al. (Nat. Biotechnol. 1996 June; 14(6): 745-50) or Frame et al. (Plant Physiol. 2002 May; 129(1): 13-22), which disclosures are incorporated by reference herein as if fully set forth.

Generally after transformation, plant cells or cell groupings are selected for the presence of one or more markers which are encoded by plant-expressible genes co-transferred with the gene of interest, following which the transformed material is regenerated into a whole plant.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced in the parent by the methods according to the invention. The invention also includes host cells containing an isolated CDKD-encoding nucleic acid. Preferred host cells according to the invention are plant cells. The invention also extends to harvestable parts of a plant such as but not limited to seeds, leaves, fruits, flowers, rhizomes, tubers and bulbs.

The present invention also encompasses the use of nucleic acids encoding CDKDs and the use of CDKD polypeptides.

One such use of course relates to the use of a CDKD in increasing plant yield, in particular in increasing seed yield. The seed yield may include one or more of the following: increased number of filled seeds, increased seed weight, increased harvest index and increased TKW, among others. The CDKD may be a nucleic acid as represented by SEQ ID NO: 1 or a functional variant thereof as hereinbefore defined; or the CDKD may be an amino acid as represented by SEQ ID NO: 2 or a functional variant thereof as hereinbefore defined.

Nucleic acids encoding CDKDs and CDKD polypeptides may also find use in breeding programmes. The CDKD may be a nucleic acid as represented by SEQ ID NO: 1 or a functional variant thereof as hereinbefore defined; or the CDKD may be an amino acid as represented by SEQ ID NO: 2 or a functional variant thereof as hereinbefore defined. For example, the CDKD-encoding nucleic acid or a functional variant thereof may be on a chromosome (or a part thereof), preferably together with one or more related family members. In an example of such a breeding programme, a DNA marker is identified which may be genetically linked to a nucleic acid encoding a CDKD protein or a functional variant thereof. This DNA marker may then used in breeding programs to select plants having increased yield.

Allelic variants of a CDKD may also be used in conventional breeding programmes, such as in marker-assisted breeding. Such breeding programmes sometimes require the introduction of allelic variations in the plants by mutagenic treatment of a plant. One suitable mutagenic method is EMS mutagenesis. Identification of allelic variants then takes place by, for example, PCR. This is followed by a selection step for selection of superior allelic variants of the sequence in question and which give increased plant yield. Selection is typically carried out by monitoring yield of plants containing different allelic variants of the sequence in question, for example, different allelic variants of SEQ ID NO: 1. Monitoring yield can be done in a greenhouse or in the field. Further optional steps include crossing plants, in which the superior allelic variant was identified, with another plant. This could be used, for example, to make a combination of interesting phenotypic features.

Nucleic acids encoding CDKDs and CDKD polypeptides may also find use as growth regulators. The CDKD may be a nucleic acid as represented by SEQ ID NO: 1 or a functional variant thereof as hereinbefore defined; or the CDKD may be an amino acid as represented by SEQ ID NO: 2 or a functional variant thereof as hereinbefore defined. Since these CDKDs are useful in increasing yield of plants, the CDKDs would also be useful growth regulators, such as herbicides or growth stimulators. The present invention therefore provides a composition comprising a CDKD, together with a suitable carrier, diluent or excipient, for use as a growth regulator.

The methods according to the invention may also be performed without introducing a nucleic acid encoding a CDKD into a plant. This may be achieved by introducing a genetic modification (preferably in the locus of a CDKD-encoding gene). The locus of a gene as defined herein is taken to mean a genomic region, which includes the gene of interest and 10 KB up- or down stream of the coding region.

The genetic modification may be introduced, for example, by any one (or more) of the following methods: TDNA activation, tilling, site-directed mutagenesis, homologous recombination or, as discussed hereinabove, by introducing and expressing in a plant (cell) a CDKD-encoding nucleic acid.

T-DNA activation tagging (Hayashi et al. Science (1992) 1350-1353) involves insertion of T-DNA usually containing a promoter (may also be a translation enhancer or an intron), in the genomic region of the gene of interest or 10 KB up- or down stream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to overexpression of genes near to the inserted T-DNA. The resulting transgenic plants show dominant phenotypes due to overexpression of genes close to the introduced promoter. The promoter to be introduced may be any promoter capable of directing expression of a gene in the desired organism, in this case a plant. For example, constitutive, tissue-preferred, cell type-preferred and inducible promoters are all suitable for use in T-DNA activation.

A genetic modification may also be introduced in the locus of a CDKD-encoding nucleic acid/gene using the technique of TILLING (Targeted Induced Local Lesions IN Genomes). This is a mutagenesis technology useful to generate and/or identify, and to eventually isolate mutagenised variants of a CDKD-encoding nucleic acid capable of exhibiting CDKD biological activity. TILLING also allows selection of plants carrying such mutant variants. These mutant variants may even exhibit higher CDKD activity than that exhibited by the gene in its natural form. TILLNG combines high-density mutagenesis with high-throughput screening methods. The steps typically followed in TILLING are: (a) EMS mutagenesis (Redei and Koncz, 1992; Feldmann et al., 1994; Lightner and Caspar, 1998); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum Nat Biotechnol. 2000 April; 18(4):455-7, reviewed by Stemple 2004 (TILLING-a high-throughput harvest for functional genomics. Nat Rev Genet. 2004 February; 5(2):145-50)).

Site directed mutagenesis may be used to generate variants of CDKD-encoding nucleic acids. Several methods are available to achieve site directed mutagenesis, the most common being PCR based methods (current protocols in molecular biology. Wiley Eds. http://wvw.4ulr.com/products/current-protocols/index.html).

TDNA activation, TILLING and site-directed mutagenesis are examples of technologies that enable the generation of novel alleles and CDKD variants.

Homologous recombination allows introduction in a genome of a selected nucleic acid at a defined selected position. Homologous recombination is a standard technology used routinely in biological sciences for lower organisms such as yeast or the moss physcomitrella. Methods for performing homologous recombination in plants have been described not only for model plants (Offringa et al. Extrachromosomal homologous recombination and gene targeting in plant cells after *Agrobacterium*-mediated transformation. 1990 EMBO J. 1990 October; 9(10):3077-84) but also for crop plants, for example rice (Terada R, Urawa H, Inagaki Y, Tsugane K, Iida S. Efficient gene targeting by homologous recombination in rice. Nat Biotechnol. 2002. Iida and Terada: A tale of two integrations, transgene and T-DNA: gene targeting by homologous recombination in rice. Curr Opin Biotechnol. 2004 April; 15(2):132-8). The nucleic acid to be targeted (which may be a CDKD-encoding nucleic acid or variant thereof as hereinbefore defined) need not be targeted to the locus of a CDKD-encoding gene, but may be introduced in, for example, regions of high expression. The nucleic acid to be targeted may be an improved allele used to replace the endogenous gene or may be introduced in addition to the endogenous gene.

The methods according to the present invention result in plants having increased yield, as described hereinbefore. These advantageous yield effects may also be combined with other economically advantageous traits, such as further yield-enhancing traits, tolerance to various stresses, traits modifying various architectural features and/or biochemical and/or physiological features.

DESCRIPTION OF FIGURES

The present invention will now be described with reference to the following figures in which:

FIG. 3 details examples of sequences useful in performing the methods according to the present invention.

EXAMPLES

The present invention will now be described with reference to the following examples, which are by way of illustration alone.

DNA manipulation: unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfase (1993) by R. D. D. Croy, published by BIOS Scientific Publications Ltd (UK) and Blackwell Scientific Publications (UK).

Example 1

Gene Cloning

The *Arabidopsis* CDKD1;1 was amplified by PCR using as template an *Arabidopsis thaliana* seedling cDNA library (Invitrogen, Paisley, UK). After reverse transcription of RNA extracted from seedlings, the cDNAs were cloned into pCMV Sport 6.0. Average insert size of the bank was 1.5 kb, and original number of clones was of $1.59 \times 10^7$ cfu. Original titer was determined to be $9.6 \times 10^5$ cfu/ml, after first amplification of $6 \times 10^{11}$ cfu/ml. After plasmid extraction, 200 ng of template was used in a 50 µl PCR mix. Primers prm2676 (sense, start codon in bold, AttB1 site in italic: 5' GGGGA-CAAGTTTGTACAAAAAAGCAGGCTTCACA-ATG-GAACAGCCGAAGAAAG 3'; SEQ ID NO: 4) and prm2677 (reverse, complementary, stop codon in bold, AttB2 site in italic: 5' GGGGACCACTTTGTACAAGAAAGCTGGGT-CCTATAGGAACTCGAGATCAAGTT 3'; SEQ ID NO: 5), which include the AttB sites for Gateway recombination, were used for PCR amplification. PCR was performed using Hifi Taq DNA polymerase in standard conditions. A PCR fragment of 1256 by was amplified and purified also using standard methods. The first step of the Gateway procedure, the BP reaction, was then performed, during which the PCR fragment recombines in vivo with the pDONR201 plasmid to produce, according to the Gateway terminology, an "entry clone", p2777. Plasmid pDONR201 was purchased from Invitrogen, as part of the Gateway® technology.

Example 2

Vector Construction

The entry clone p2777 was subsequently used in an LR reaction with p0640, a destination vector used for *Oryza sativa* transformation. This vector contained within the T-DNA borders: a plant selectable marker; a screenable marker; and a Gateway cassette intended for LR in vivo recombination with the sequence of interest already cloned in the entry clone. A rice GOS2 promoter for constitutive expression was located upstream of the Gateway cassette.

Figure 1:
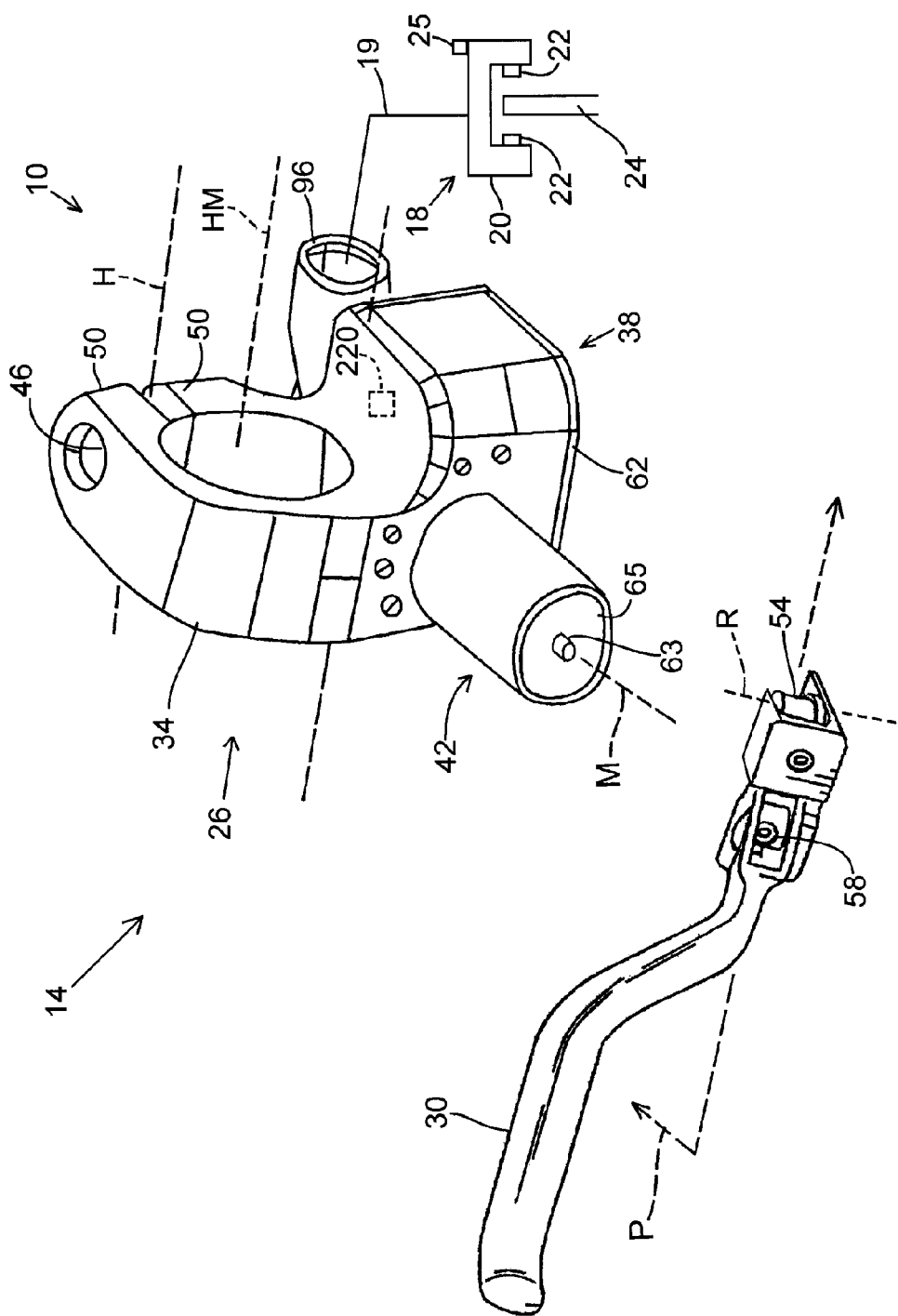
FIG. 1 is a tree showing various plant CDKs. Full-length CDK protein sequences were aligned using the "ClustalX1.81" software with its default parameters. A neighbour-joining tree was calculated from this alignment using "ClustalX1.81" with its default parameters. The tree was drawn using the "drawgram" program of the "Phylip3.5" package with its default parameters.
Figure 2:
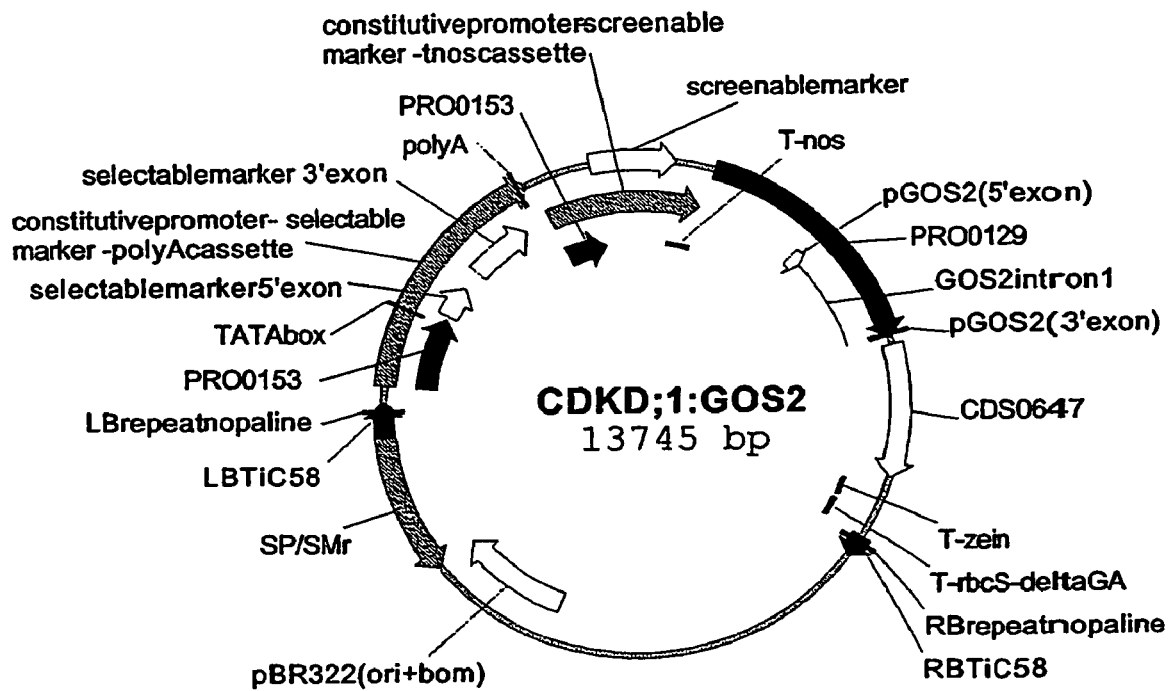
FIG. 2 shows a binary vector for expression in *Oryza sativa* of the *Arabidopsis thaliana* CDKD;1 gene under the control of a GOS2 promoter.

After the LR recombination step, the resulting expression vector as shown in FIG. 2 (CDK D1;1::GOS2—upregulation) was transformed into *Agrobacterium* and subsequently into *Oryza sativa* plants. Transformed rice plants were allowed to grow and were then examined for the parameters described in Example 3.

Example 3

Evaluation and Results

Approximately 15 to 20 independent T0 rice transformants were generated. The primary transformants were transferred from tissue culture chambers to a greenhouse for growing and harvest of T1 seed. 6 events, of which the T1 progeny segregated 3:1 for presence/absence of the transgene, were retained. For each of these events, approximately 10 T1 seedlings containing the transgene (hetero- and homo-zygotes), and approximately 10 T1 seedlings lacking the transgene (nullizygotes), were selected by monitoring visual marker expression.

Statistical Analysis: t-Test and F-Test

A two factor ANOVA (analysis of variants) was used as a statistical model for the overall evaluation of plant phenotypic characteristics. An F-test was carried out on all the parameters measured of all the plants of all the events transformed with the gene of the present invention. The F-test was carried out to check for an effect of the gene over all the transformation events and to verify for an overall effect of the gene, also known as a global gene effect. The threshold for significance for a true global gene effect was set at a 5% probability level for the F-test. A significant F-test value points to a gene effect, meaning that it is not only the presence or position of the gene that is causing the differences in phenotype.

To check for an effect of the genes within an event, i.e., for a line-specific effect, a t-test was performed within each event using data sets from the transgenic plants and the corresponding null plants. "Null plants" or "Null segregants" are the plants treated in the same way as transgenic plants, but from which the transgene has segregated. Null plants may also be described as homozygous negative transformants. The threshold for significance for the t-test was set at a 10% probability level. Within one population of 5 transformation events, some events can be under or above this t-test threshold. This is based on the hypothesis that a gene might only have an effect in certain positions in the genome, and that the occurrence of this position-dependent effect is not uncommon. This kind of gene effect is also known as a line effect of the gene. The p-value was obtained by comparing the t-value to the t-distribution or alternatively, by comparing the F-value to the F-distribution. The p-value then stands for the probability that the null hypothesis (null hypothesis being "there is no effect of the transgene") is correct.

4.1 Vegetative Growth Measurements:

The selected T1 plants (approximately 10 with the transgene and approximately 10 without the transgene) were transferred to a greenhouse. Each plant received a unique barcode label to link unambiguously the phenotyping data to the corresponding plant. The selected T1 plants were grown on soil in 10 cm diameter pots under the following environmental settings: photoperiod=11.5 h, daylight intensity=30,000 lux or more, daytime temperature=28° C. or higher, night time temperature=22° C., relative humidity=60-70%. Transgenic plants and the corresponding nullizygotes were grown side-by-side at random positions. From the stage of sowing until the stage of maturity each plant was passed several times through a digital imaging cabinet and imaged. At each time point digital images (2048×1536 pixels, 16 million colours) were taken of each plant from at least 6 different angles. The parameters described below were derived in an automated way from all the digital images of all the plants, using image analysis software.

4.1.1 Aboveground Plant Area

Plant aboveground area was determined by counting the total number of pixels from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground. The best 3 lines of the T1 evaluation were then evaluated in the T2 round. The results of the T2 evaluation are shown in Table 1 below. As shown, one of the lines shows a statistically significant increase in aboveground area (with p-value from the t-test of 0.0107) compared to corresponding nullizygotes.

TABLE 1

Aboveground Area

| Line | TR | null | dif | % dif | p-value |
|---|---|---|---|---|---|
| 0010A | 32153 | 27611 | 4541 | 16 | 0.1555 |
| 0009A | 38565 | 30317 | 8249 | 27 | 0.0107 |
| 0007A | 53336 | 56624 | −3288 | −6 | 0.3027 |
| Overall | 41351 | 38184 | 3167 | 8 | 0.0748 |

Each row corresponds to one event, for which the aboveground area was determined for the transgenics (TR) and the null lines (null), expressed in units. The numeric difference between the positive plants and the negative plants is given (dif) as well as the percentage of difference between these plants (% dif). P-value stands for the probability produced by the t-test for each plant line. The last row presents the average numbers for all events. There, the p-value stands for the p-value derived from the F-test.

4.2 Seed-Related Parameter Measurements

The mature primary panicles were harvested, bagged, barcode-labelled and then dried for three days in the oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. This procedure resulted in the set of seed-related parameters described below.

4.2.0 Number of Filled Seeds

The number of filled seeds was determined by counting the number of filled husks that remained after the separation step. Again, 3 of the best plants from the T1 evaluation were taken to the T2 round. The results of the T2 evaluation are shown in Table 2 below. As shown, 2 of the lines showed a significant increase in the number of filled seeds of transgenic plants relative to the number of filled seeds of corresponding non-transgenic plants. There was also an overall gene effect as concluded by the significant p value from the F-test of 0.

TABLE 2

Number of Filled Seeds

| Line | TR | null | dif | % dif | p-value |
|---|---|---|---|---|---|
| 0010A | 119 | 82.3 | 36.65 | 45 | 0.6588 |
| 0009A | 146.6 | 18.7 | 127.85 | 684 | 0 |
| 0007A | 198.6 | 207.7 | −9.15 | −4 | 0.7586 |
| Overall | 154.7 | 102.9 | 51.78 | 50 | 0 |

Each row corresponds to one event, for which the number of filled seeds was determined for the transgenics (TR) and the null lines (null), expressed in units. The numeric difference between the positive plants and the negative plants is given (dif) as well as the percentage of difference between these plants (% dif). P-value stands for the probability produced by the t-test for each plant line. The last row presents the average numbers for all events. There, the p-value stands for the p-value derived from the F-test.

4.2.1 Total Seed Yield Per Plant

The total seed yield was measured by weighing all filled husks harvested from a plant. Again, 3 of the best plants from the T1 evaluation were taken to the T2 round. The results of the T2 evaluation are shown in Table 3 below. As shown, 2 of the lines showed a significant increase in seed weight for transgenic plants relative to the seed weight of corresponding non-transgenic plants. There was also an overall gene effect as concluded by the significant p value from the F-test of 0.

TABLE 3

Total Seed Weight

| Line | TR | null | dif | % diff | p-value |
|---|---|---|---|---|---|
| 0010A | 3.1 | 2.1 | 0.94 | 44 | 0.0745 |
| 0009A | 4 | 0.5 | 3.51 | 702 | 0 |
| 0007A | 5.3 | 5.6 | −0.36 | −6 | 0.6589 |
| Overall | 4.1 | 2.8 | 1.35 | 49 | 0 |

Each row corresponds to one event, for which the total seed weight was determined for the transgenics (TR) and the null lines (null), expressed in units. The numeric difference between the positive plants and the negative plants is given (dif) as well as the percentage of difference between these plants (% dif). P-value stands for the probability produced by the t-test for each plant line. The last row presents the average numbers for all events. There, the p-value stands for the p-value derived from the F-test.

4.2.3 Harvest Index of Plants

The harvest index in the present invention is defined as the ratio between the total seed yield and the above ground area ($mm^2$), multiplied by a factor 106. Three of the best plants from the T1 evaluation were taken to the T2 round and the results of the T2 evaluation are shown in Table 4 below. As shown, 1 line showed an increased harvest index for transgenic plants relative to the harvest index of corresponding non-transgenic plants, with a p value from the t-test of 0. An overall gene effect was also evident with a p-value from the F-test of 0.

TABLE 4

Harvest Index

| Line | TR | null | dif | % dif | p-value |
|---|---|---|---|---|---|
| 0010A | 95.8 | 86.3 | 9.47 | 11 | 0.3758 |
| 0009A | 104.1 | 18.1 | 85.93 | 473 | 0 |
| 0007A | 94.6 | 94.7 | −0.14 | −0 | 0.9885 |
| Overall | 97.9 | 68.6 | 29.27 | 43 | 0 |

Each row corresponds to one event, for which the harvest index was determined for the transgenics (TR) and the null lines (null), expressed in units. The numeric difference between the positive plants and the negative plants is given (dif) as well as the percentage of difference between these plants (% dif). P-value stands for the probability produced by the t-test for each plant fine. The last row presents the average numbers for all events. There, the p-value stands for the p-value derived from the F-test.

4.2.4 Thousand Kernel Weight (TKW)

This parameter is extrapolated from the number of filled seeds counted, and their total weight. Three of the best plants from the T1 evaluation were taken to the T2 round and the results of the T2 evaluation are shown in Table 5 below. As shown, one of the lines showed an increase in the TKW for transgenic plants relative to corresponding non-transgenic plants, with a p value from the t-test of 0.0455.

TABLE 5

| TKW | | | | | |
|---|---|---|---|---|---|
| Line | TR | null | dif | % dif | p-value |
| OS0934-0010A | 25.1 | 24.6 | 0.52 | 2 | 0.3453 |
| OS0934-0009A | 26.1 | 24.8 | 1.23 | 5 | 0.0455 |

TABLE 5-continued

| TKW | | | | | |
|---|---|---|---|---|---|
| Line | TR | null | dif | % dif | p-value |
| OS0934-0007A | 26.5 | 26.8 | −0.3 | −1 | 0.5609 |
| Overall | 25.9 | 25.5 | 0.39 | 12 | 0.2473 |

Each row corresponds to one event, for which the TKW was determined for the transgenics (TR) and the null lines (null), expressed in units. The numeric difference between the positive plants and the negative plants is given (dif) as well as the percentage of difference between these plants (% dif). P-value stands for the probability produced by the t-test for each plant line. The last row presents the average numbers for all events. There, the p-value stands for the p-value derived from the F-test.

The invention claimed is:

1. A method for increasing seed yield relative to corresponding wild type plants, comprising introducing into a plant a nucleic acid encoding a D-type Cyclin Dependent Kinase (CDKD) resulting in a transgenic plant having increased seed yield relative to a corresponding wild type plant; and selecting a transgenic plant having increased seed yield relative to a corresponding wild type plant.

2. The method according to claim 1, wherein said increased seed yield is selected from the group consisting of (i) increased seed biomass; (ii) increased number of seeds; (iii) increased seed size; (iv) increased seed volume; (v) increased harvest index; and (vi) increased thousand kernel weight (TKW).

3. The method according to claim 1, wherein said nucleic acid encodes a CDKD which comprises an NXTALRE motif (SEQ ID NO: 6) and a catalytic kinase domain and wherein said nucleic acid is obtained from a plant.

4. The method according to claim 1, wherein the nucleic acid comprises a nucleic acid sequence selected from the group consisting of:
 (i) a nucleic acid sequence represented by the sequence of SEQ ID NO: 1;
 (ii) a portion of the nucleic acid sequence represented by the sequence of SEQ ID NO: 1 which encodes a CDKD comprising an NXTALRE motif (SEQ ID NO: 6) and a catalytic kinase domain;

(iii) a nucleic acid sequence which hybridizes to the complement of the full-length nucleic acid sequence represented by the sequence of SEQ ID NO: 1 under stringent conditions of 5× sodium chloride/sodium citrate (SSC) at 55 to 65° C. followed by one or more washes in 0.2×SSC at 55 to 65° C. and which encodes a CDKD comprising an NXTALRE motif (SEQ ID NO: 6) and a catalytic kinase domain; and (iv) a nucleic acid sequence which encodes a CDKD comprising an NXTALRE motif (SEQ ID NO: 6) and a catalytic kinase domain;

or wherein the CDKD comprises the amino acid sequence of SEQ ID NO: 2 or an amino acid sequence comprising an NXTALRE motif (SEQ ID NO: 6) and a catalytic kinase domain.

5. The method according to claim 1, wherein said nucleic acid sequence encoding a CDKD is overexpressed in a plant.

6. The method according to claim 1, wherein expression of said nucleic acid encoding a CDKD is driven by a constitutive promoter.

7. A method for the production of a transgenic plant having increased seed yield, which method comprises:
   (i) introducing into a plant or plant cell a D-type Cyclin Dependent Kinase (CDKD)-encoding nucleic acid or a nucleic acid which encodes a CDKD comprising an NXTALRE motif (SEQ ID NO: 6) and a catalytic kinase domain;
   (ii) cultivating the plant cell under conditions promoting regeneration and mature plant growth resulting in a transgenic plant having increased seed yield relative to a corresponding wild type plant; and
   (iii) selecting a plant having increased seed yield relative to a corresponding wild type plant.

8. A transgenic plant obtained by the method of claim 1.

9. A construct comprising:
   (i) a D-type Cyclin Dependent Kinase (CDKD)-encoding nucleic acid or a nucleic acid which encodes a CDKD comprising an NXTALRE motif (SEQ ID NO: 6) and a catalytic kinase domain, wherein the nucleic acid comprises the nucleic acid sequence of SEQ ID NO: 1, a nucleic acid sequence encoding the amino acid sequence of SEQ ID NO: 2, or a nucleic acid sequence encoding a polypeptide comprising an amino acid sequence having at least 95% identity to SEQ ID NO: 2;
   (ii) one or more control sequence capable of driving expression of the nucleic acid sequence of (i) which comprises at least a GOS2 promoter; and optionally
   (iii) a transcription termination sequence.

10. A plant transformed with the construct according to claim 9.

11. A transgenic plant having increased seed yield relative to a corresponding wild type plant, wherein said plant comprises an isolated nucleic acid encoding a D-type Cyclin Dependent Kinase (CDKD) or a nucleic acid which encodes a CDKD comprising an NXTALRE motif (SEQ ID NO: 6) and a catalytic kinase domain.

12. The transgenic plant according to claim 11, wherein said plant is a monocotyledonous plant.

13. Harvestable parts including seed of the plant according to claim 8, wherein the harvestable parts comprise the nucleic acid.

14. The method according to claim 1, wherein said seed yield includes one or more of the following: increased number of filled seeds, increased seed weight, increased harvest index and increased thousand kernel weight (TKW).

15. The method according to claim 1, wherein said CDKD is encoded by a nucleic acid comprising the nucleic acid sequence as represented by SEQ ID NO: 1 or a nucleic acid which encodes a CDKD comprising an NXTALRE motif (SEQ ID NO: 6) and a catalytic kinase domain, or wherein said CDKD comprises the amino acid sequence as represented by SEQ ID NO: 2 or an amino acid sequence comprising an NXTALRE motif (SEQ ID NO: 6) and a catalytic kinase domain.

16. The transgenic plant according to claim 10, wherein said plant is selected from the group consisting of sugar cane, rice, maize, wheat, barley, millet, rye, sorghum or oats.

17. The transgenic plant according to claim 12, wherein said monocotyledonous plant is a cereal.

18. The transgenic plant of claim 11, wherein the nucleic acid comprises the nucleic acid sequence of SEQ ID NO: 1, a nucleic acid sequence encoding the amino acid sequence of SEQ ID NO: 2, or a nucleic acid sequence encoding a polypeptide comprising an amino acid sequence having at least 95% identity to SEQ ID NO: 2.

19. A method for obtaining plants having increased seed yield relative to a corresponding wild type plant comprising
   (a) cultivating a transgenic plant or transgenic seed, which plant or seed are transgenic for a D-type Cyclin Dependent Kinase (CDKD)-encoding nucleic acid or a nucleic acid which encodes a CDKD comprising an NXTALRE motif (SEQ ID NO: 6) and a catalytic kinase domain;
   (b) obtaining a transgenic plant having increased seed yield relative to a corresponding wild type plant; and optionally
   (c) harvesting transgenic seed from the transgenic plant obtained in step (b).

20. A plant comprising the construct of claim 9.

* * * * *

SEQUENCE LISTING

<160> NUMBER OF SEQ ID NOS: 11

<210> SEQ ID NO 1
<211> LENGTH: 1256
<212> TYPE: DNA
<213> ORGANISM: Arabidopsis thaliana

<400> SEQUENCE: 1

```
atggaacagc cgaagaaagt tgctgatagg tatctaaagc gagaggttct tggtcaaggt      60
acttatggag tcgtcttcaa agctactgat acaaagaatg gagaaactgt agcgatcaag     120
aaaataagac ttggtaaaga gaaagaaggt gtgaatgtaa cagctcttag agaaatcaaa     180
ttacttaaag agcttaagca tccacatata attgagttga ttgatgcgtt tcctcacaag     240
gagaatttgc acatcgtgtt tgagttcatg gagactgatc tcgaagcagt tatccgagat     300
cgtaatctct atctttcgcc tggtgatgtc aaatcttacc tccaaatgat attgaaaggt     360
cttgaatatt gccatggcaa atgggttctg cacagagata tgaagccaaa caacttgttg     420
ataggaccca atggacagct gaaacttgca gattttgggt tagcacgtat atttggtagc     480
ccaggtcgta agtttaccca ccaggtgttt gctagatggt atagagcacc tgaactttg      540 tttggtgcaa aacaatatga tggtgcagtt gatgtttggg ctgctggctg cattttgct      600 gaacttctat tacgcagacc atttcttcag ggaaacagtg atattgatca attaagcaaa     660
atctttgctg cctttgggac tccaaaagca gatcagtggc ctgacatgat ctgccttcct     720
gattatgtag agtatcaatt tgtccctgct ccttctttac gttctttact cccaacggtt     780
agtgaggatg ctttagattt gttgtcaaag atgttcacct atgacccaa  gtctagaata      840 tcgattcagc aggctctaaa acacaggtac ttcacatctg caccttcacc tactgaccct     900
ttaaagctcc caagaccagt ttccaagcaa gatgctaagt catctgatag taaacttgaa     960
gccattaaag tgctgtcacc agcacataag tttagaagag tgatgcctga ccgaggaaag    1020
tctggtaatg gtttcaagga ccagagtgtt gatgtcatga caagctag  ccatgatgga     1080 caagcaccaa tgtctttaga tttcaccatc ttagctgagc ggccaccaaa ccgaccaacc    1140
```

```
atcaccagtg cagatagatc tcatctgaag aggaaacttg atctcgagtt cctataggat   1200
atcgcgtaac aggcttcttc ttgacgtcgt tcttcaggtt cctatagcct atagga       1256
```

<210> SEQ ID NO 2
<211> LENGTH: 398
<212> TYPE: PRT
<213> ORGANISM: Arabidopsis thaliana

<400> SEQUENCE: 2

```
Met Glu Gln Pro Lys Lys Val Ala Asp Arg Tyr Leu Lys Arg Glu Val
 1               5                  10                  15

Leu Gly Gln Gly Thr Tyr Gly Val Val Phe Lys Ala Thr Asp Thr Lys
            20                  25                  30

Asn Gly Glu Thr Val Ala Ile Lys Lys Ile Arg Leu Gly Lys Glu Lys
        35                  40                  45

Glu Gly Val Asn Val Thr Ala Leu Arg Glu Ile Lys Leu Leu Lys Glu
    50                  55                  60

Leu Lys His Pro His Ile Ile Glu Leu Ile Asp Ala Phe Pro His Lys
65                  70                  75                  80

Glu Asn Leu His Ile Val Phe Glu Phe Met Glu Thr Asp Leu Glu Ala
                85                  90                  95

Val Ile Arg Asp Arg Asn Leu Tyr Leu Ser Pro Gly Asp Val Lys Ser
            100                 105                 110

Tyr Leu Gln Met Ile Leu Lys Gly Leu Glu Tyr Cys His Gly Lys Trp
        115                 120                 125

Val Leu His Arg Asp Met Lys Pro Asn Asn Leu Leu Ile Gly Pro Asn
    130                 135                 140

Gly Gln Leu Lys Leu Ala Asp Phe Gly Leu Ala Arg Ile Phe Gly Ser
145                 150                 155                 160

Pro Gly Arg Lys Phe Thr His Gln Val Phe Ala Arg Trp Tyr Arg Ala
                165                 170                 175

Pro Glu Leu Leu Phe Gly Ala Lys Gln Tyr Asp Gly Ala Val Asp Val
            180                 185                 190

Trp Ala Ala Gly Cys Ile Phe Ala Glu Leu Leu Leu Arg Arg Pro Phe
        195                 200                 205

Leu Gln Gly Asn Ser Asp Ile Asp Gln Leu Ser Lys Ile Phe Ala Ala
    210                 215                 220

Phe Gly Thr Pro Lys Ala Asp Gln Trp Pro Asp Met Ile Cys Leu Pro
225                 230                 235                 240

Asp Tyr Val Glu Tyr Gln Phe Val Pro Ala Pro Ser Leu Arg Ser Leu
                245                 250                 255

Leu Pro Thr Val Ser Glu Asp Ala Leu Asp Leu Leu Ser Lys Met Phe
            260                 265                 270

Thr Tyr Asp Pro Lys Ser Arg Ile Ser Ile Gln Gln Ala Leu Lys His
        275                 280                 285

Arg Tyr Phe Thr Ser Ala Pro Ser Pro Thr Asp Pro Leu Lys Leu Pro
    290                 295                 300

Arg Pro Val Ser Lys Gln Asp Ala Lys Ser Ser Asp Ser Lys Leu Glu
305                 310                 315                 320

Ala Ile Lys Val Leu Ser Pro Ala His Lys Phe Arg Arg Val Met Pro
                325                 330                 335

Asp Arg Gly Lys Ser Gly Asn Gly Phe Lys Asp Gln Ser Val Asp Val
            340                 345                 350
```

```
Met Arg Gln Ala Ser His Asp Gly Gln Ala Pro Met Ser Leu Asp Phe
        355                 360                 365

Thr Ile Leu Ala Glu Arg Pro Pro Asn Arg Pro Thr Ile Thr Ser Ala
370                 375                 380

Asp Arg Ser His Leu Lys Arg Lys Leu Asp Leu Glu Phe Leu
385                 390                 395

<210> SEQ ID NO 3
<211> LENGTH: 2193
<212> TYPE: DNA
<213> ORGANISM: Oryza sativa

<400> SEQUENCE: 3
aatccgaaaa gtttctgcac cgttttcacc ccctaactaa caatataggg aacgtgtgct      60
aaatataaaa tgagacctta tatgtagc gctgataact agaactatgc aagaaaaact      120
catccaccta ctttagtggc aatcgggcta aataaaaaag agtcgctaca ctagtttcgt     180
tttccttagt aattaagtgg gaaaatgaaa tcattattgc ttagaatata cgttcacatc     240
tctgtcatga agttaaatta ttcgaggtag ccataattgt catcaaactc ttcttgaata     300
aaaaaatctt tctagctgaa ctcaatgggt aaagagagag atttttttta aaaaatag      360 atgaagatat tctgaacgta ttggcaaaga tttaaacata taattatata attttatagt    420
ttgtgcattc gtcatatcgc acatcattaa ggacatgtct tactccatcc caattttat     480 ttagtaatta aagacaattg acttatttt attatttatc ttttttcgat tagatgcaag     540
gtacttacgc acacactttg tgctcatgtg catgtgtgag tgcacctcct caatacacgt    600
tcaactagca acacatctct aatatcactc gcctatttaa tacatttagg tagcaatatc    660
tgaattcaag cactccacca tcaccagacc actttaata atatctaaaa tacaaaaaat    720
aattttacag aatagcatga aaagtatgaa acgaactatt taggttttc acatacaaaa    780 aaaaaagaa ttttgctcgt gcgcgagcgc caatctccca tattgggcac acaggcaaca    840
acagagtggc tgcccacaga caacccaca aaacgatg atctaacgga ggacagcaag       900
tccgcaacaa ccttttaaca gcaggctttg cggccaggag agaggaggag aggcaaagaa    960
aaccaagcat cctcctcctc ccatctataa attcctcccc ccttttcccc tctctata       1020 ggaggcatcc aagccaagaa gagggagagc accaaggaca cgcgactagc agaagccgag    1080
cgaccgcctt cttcgatcca tatcttccgg tcgagttctt ggtcgatctc ttccctcctc    1140
cacctcctcc tcacgggta tgtgcccttc ggttgttctt ggatttattg ttctaggttg     1200
tgtagtacgg gcgttgatgt taggaaaggg gatctgtatc tgtgatgatt cctgttcttg    1260
gatttgggat agagggttc ttgatgttgc atgttatcgg ttcggtttga ttagtagtat     1320
ggttttcaat cgtctggaga gctctatgga aatgaaatgg tttagggtac ggaatcttgc    1380
gattttgtga gtacctttg tttgaggtaa atcagagca ccggtgattt tgcttggtgt     1440
aataaaagta cggttgtttg gtcctcgatt ctggtagtga tgcttctcga tttgacgaag    1500
ctatcctttg tttattccct attgaacaaa aataatccaa ctttgaagac ggtcccgttg    1560
atgagattga atgattgatt cttaagcctg tccaaaattt cgcagctggc ttgtttagat    1620
acagtagtcc ccatcacgaa attcatggaa acagttataa tcctcaggaa caggggattc    1680
cctgttcttc cgatttgctt tagtcccaga attttttttc ccaaatatct taaaaagtca    1740 cttttctggtt cagttcaatg aattgattgc tacaaataat gcttttatag cgttatccta    1800
gctgtagttc agttaatagg taatacccct atagtttagt caggagaaga acttatccga    1860
```

```
tttctgatct ccatttttaa ttatatgaaa tgaactgtag cataagcagt attcatttgg    1920 attattttt ttattagctc tcaccccttc attattctga gctgaaagtc tggcatgaac    1980
tgtcctcaat tttgttttca aattcacatc gattatctat gcattatcct cttgtatcta    2040
cctgtagaag tttcttttg gttattcctt gactgcttga ttacagaaag aaatttatga    2100
agctgtaatc gggatagtta tactgcttgt tcttatgatt catttccttt gtgcagttct    2160
tggtgtagct tgccactttc accagcaaag ttc                                2193
```

```
<210> SEQ ID NO 4
<211> LENGTH: 53
<212> TYPE: DNA
<213> ORGANISM: Artificial sequence
<220> FEATURE:
<223> OTHER INFORMATION: primer prm2676

<400> SEQUENCE: 4
ggggacaagt ttgtacaaaa aagcaggctt cacaatggaa cagccgaaga aag           53

<210> SEQ ID NO 5
<211> LENGTH: 53
<212> TYPE: DNA
<213> ORGANISM: Artificial sequence
<220> FEATURE:
<223> OTHER INFORMATION: primer prm2677

<400> SEQUENCE: 5
ggggaccact ttgtacaaga aagctgggtc ctataggaac tcgagatcaa gtt           53

<210> SEQ ID NO 6
<211> LENGTH: 7
<212> TYPE: PRT
<213> ORGANISM: Artificial Sequence
<220> FEATURE:
<223> OTHER INFORMATION: Motif from a D-type Cyclin Dependent Kinase
<220> FEATURE:
<221> NAME/KEY: misc_feature
<222> LOCATION: (2)..(2)
<223> OTHER INFORMATION: Xaa can be any naturally occurring amino acid

<400> SEQUENCE: 6

Asn Xaa Thr Ala Leu Arg Glu
 1               5

<210> SEQ ID NO 7
<211> LENGTH: 7
<212> TYPE: PRT
<213> ORGANISM: Artificial Sequence
<220> FEATURE:
<223> OTHER INFORMATION: Motif from an A-type Cyclin-Dependent Kinase

<400> SEQUENCE: 7

Pro Ser Thr Ala Ile Arg Glu
 1               5

<210> SEQ ID NO 8
<211> LENGTH: 7
<212> TYPE: PRT
<213> ORGANISM: Artificial Sequence
<220> FEATURE:
<223> OTHER INFORMATION: Motif from a B-type Cyclin-Dependent Kinase
<220> FEATURE:
<221> NAME/KEY: misc_feature
<222> LOCATION: (2)..(2)
<223> OTHER INFORMATION: Xaa is Pro or Ser
```

```
<220> FEATURE:
<221> NAME/KEY: misc_feature
<222> LOCATION: (4)..(4)
<223> OTHER INFORMATION: Xaa is Ala or Thr
      220>
<221> NAME/KEY: misc_feature
<222> LOCATION: (5)..(5)
<223> OTHER INFORMATION: Xaa is Leu or Met

<400> SEQUENCE: 8

Pro Xaa Thr Xaa Xaa Arg Glu
1               5

<210> SEQ ID NO 9
<211> LENGTH: 7
<212> TYPE: PRT
<213> ORGANISM: Artificial Sequence
<220> FEATURE:
<223> OTHER INFORMATION: Motif from C-type Cyclin-Dependent Kinase

<400> SEQUENCE: 9

Pro Ile Thr Ala Ile Arg Glu
1               5

<210> SEQ ID NO 10
<211> LENGTH: 6
<212> TYPE: PRT
<213> ORGANISM: Artificial Sequence
<220> FEATURE:
<223> OTHER INFORMATION: Motif from E-type Cyclin-Dependent Kinase

<400> SEQUENCE: 10

Ser Pro Thr Ala Arg Glu
1               5

<210> SEQ ID NO 11
<211> LENGTH: 6
<212> TYPE: PRT
<213> ORGANISM: Artificial Sequence
<220> FEATURE:
<223> OTHER INFORMATION: Motif from F-type Cyclin-Dependent Kinase
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 11

Xaa Ser Ala Xaa Arg Glu
1               5
```